United States Patent [19]
Zafiroglu

[11] Patent Number: 5,468,320
[45] Date of Patent: Nov. 21, 1995

[54] PROCESS FOR ELASTIC NONWOVEN UNDERGARMENT WITH A STITCHBONDED OUTER SHELL

[75] Inventor: Dimitri P. Zafiroglu, Wilmington, Del.

[73] Assignee: E. I. DuPont de Nemours and Company, Wilmington, Del.

[21] Appl. No.: 224,347

[22] Filed: Apr. 7, 1994

Related U.S. Application Data

[63] Continuation-in-part of Ser. No. 907,902, Jul. 6, 1992, abandoned.

[51] Int. Cl.$^6$ .............................. B32B 31/18; D04B 23/08; A61F 13/16
[52] U.S. Cl. .................... 156/148; 156/161; 156/229; 156/251; 604/384; 604/385.1
[58] Field of Search ........................ 156/161, 163, 156/164, 166, 167, 176, 177, 251, 229, 272.8, 73.3, 515, 582, 496, 510, 513, 525, 575, 530, 543, 148; 604/384, 385.1; 219/121.65, 121.67, 121.72

[56] References Cited

U.S. PATENT DOCUMENTS

| | | |
|---|---|---|
| 3,817,802 | 6/1974 | Meyer . |
| 4,029,535 | 6/1977 | Cannon et al. . |
| 4,496,407 | 1/1985 | Lowery et al. . |
| 4,606,964 | 8/1986 | Wideman . |
| 4,626,305 | 12/1986 | Suzuki et al. . |
| 4,701,171 | 10/1987 | Boland et al. . |
| 4,701,172 | 10/1987 | Stevens . |
| 4,701,174 | 10/1987 | Johnson . |
| 4,756,709 | 7/1988 | Stevens . |
| 4,773,238 | 9/1988 | Zafiroglu . |
| 4,998,421 | 3/1991 | Zafiroglu . |

Primary Examiner—Jeff H. Aftergut

[57] ABSTRACT

A simplified process is disclosed for making form-fitting undergarments that may include structures for absorbing and containing body exudates. The garments are cut and seamed into rectangular or trapezoidal shapes from nonwoven elastic sheet that has parallel rows of elastic strands and specific stretch and simultaneous contraction characteristics. The finished garment when stretched in the waist direction simultaneously contracts in the direction perpendicular thereto by at least 20%.

6 Claims, 4 Drawing Sheets 5,468,320

PROCESS FOR ELASTIC NONWOVEN UNDERGARMENT WITH A STITCHBONDED OUTER SHELL

RELATED APPLICATION

This is a continuation-in-part of application Ser. No. 07/907,902, filed Jul. 6, 1992, now abandoned.

BACKGROUND OF THE INVENTION

1. Field of the Invention

This invention relates a process for making an anatomically form-fitting elastic undergarment which optionally includes an absorbent structure for containment of body exudates. More particularly, the invention concerns such a process wherein particular nonwoven starting sheets are cut and seamed with minimal waste material to form a garment of rectangular or trapezoidal configuration which is flat and easy to package.

2. Description of the Prior

Disposable undergarments, panties, diapers and the like, typically comprise an outer shell having a waist opening and two leg openings. Often, as disclosed by Suzuki et al, U.S. Pat. No. 4,626,305, particular elastic elements are incorporated in the waist and leg openings to provide a tighter fit of the undergarment to its wearer's body. Processes for making such garments generally require special steps for gluing or bonding the elastic elements in place. Such special steps often reduce manufacturing speeds and increase costs.

Disposable undergarments which have stretchable outer shells, and processes for making them also are known. For example, Wideman, U.S. Pat. No. 4,606,964 describes a differentially tensioned, reticulated web of elastic material bonded to a gatherable web which is suitable for use in, among other things, the manufacture of disposable diapers, training pants for infants and panty-like garments. Stevens, U.S. Pat. No. 4,701,172, discloses such a garment having an outer shell which comprises an elastic nonwoven web of elastomeric microfibers which is joined to one or more gatherable nonwoven webs. An absorbent structure is attached to the outer shell in a way that does not restrict the stretchability of the shell. Typically, the outer shell has recoverable stretch in only one direction. Various approaches have been disclosed for achieving two way stretchability. For example, Johnson, U.S. Pat. No. 4,701,174, discloses deploying an outer shell fabric on the bias and Boland et al, U.S. Pat. No. 4,701,171 and Stevens, U.S. Pat. No. 4,756,709 disclose outer shells which have certain zones of stretchability.

An object of the present invention is to provide an improved and simplified process for making such undergarments.

SUMMARY OF THE INVENTION

The present invention provides an improved process for making an anatomically form-fitting elastic undergarment that has a stretchable outer shell which is fabricated with a waist opening and two leg openings. The process is of the type that comprises cutting and seaming an elastic nonwoven sheet to form the outer shell for the garment and optionally attaching to its inner surface an absorbent structure for containment of body exudates. The improvement of the present invention comprises: (a) the elastic nonwoven sheet comprising an array of parallel spaced-apart rows of elastic strands incorporated with a deformable substrate, the strands having a spacing in the range 1 to 8 rows per centimeter, and the elastic nonwoven sheet having an elastic stretch of at least 70% in a first direction and a simultaneous contraction in a direction perpendicular to the first direction of at least 20%, the contraction being at least 20% when the elastic stretch is 70%; (b) feeding the elastic nonwoven sheet to the cutting and seaming operations, in a direction substantially parallel to or perpendicular to the first direction of the sheet, at substantially uniform tension across the width of the sheet; and (c) selectively cutting and seaming the nonwoven sheets in a flat trapezoidal or rectangular geometry with the first direction parallel to the waist direction of the undergarment being fabricated, to form the outer shell with the parallel rows of elastic strands being positioned in substantially the same direction throughout the shell. Preferably, the elastic stretch in the first direction is in the range of 100 to 250% and the simultaneous total contraction in the direction perpendicular thereto is in the range of 25 to 60%. In one embodiment of the process the elastic nonwoven sheet is a stitchbonded nonwoven fabric having a unit weight in the range of 17 to 65 grams per square meter and comprising a substantially nonbonded fibrous layer that is stitched with elastic yarns that form the parallel rows of elastic strands, the frequency of the stitches within the rows being in the range of 1 to 8 per centimeter, preferably in the range of 2 to 5 per cm. Preferably, the rows of stitches are formed by series of tricot stitches or chain stitches or combinations thereof.

BRIEF DESCRIPTION OF THE DRAWINGS

The invention will be better understood by referring to the attached drawings wherein.

DETAILED DESCRIPTION OF PREFERRED EMBODIMENTS

The invention is further illustrated by the following description of preferred embodiments. These are included for the purposes of illustration and are not intended to limit the scope of the invention, which is defined by the appended claims.

Figure 8:
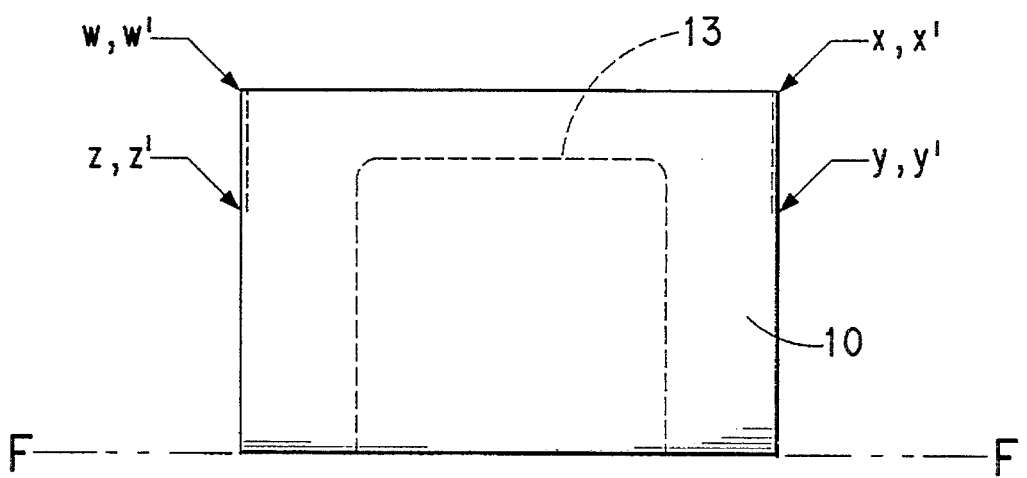
Figure 9:
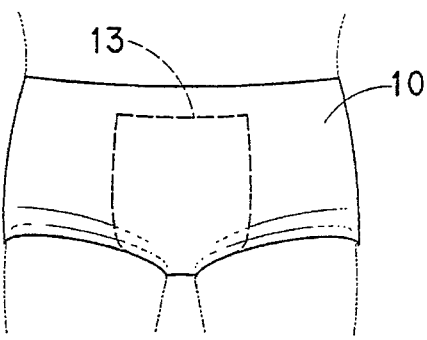
FIG. 9 illustrates an undergarment made by the process of the invention being worn, stretched in the waist while contracted perpendicular to the waist to provide a proper fit in the crotch.
Figure 11:
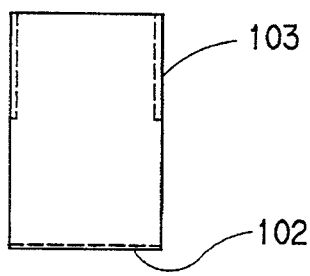
FIGS. 11 and 12 illustrate individual completed undergarments, for undergarments prepared by the process of FIGS. 2 and 10 involving two elastic nonwoven sheets, in the flat ready-for-use condition and in the "as-worn" condition, respectively.
Figure 12:
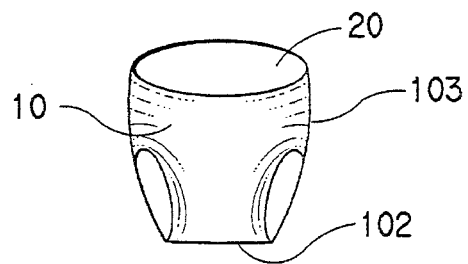

The undergarment product of the process of the present invention, as illustrated for example in FIGS. 11 and 12, has an elastic outer shell 10, 20, which includes a waist opening and two leg openings and seams formed in the sides 103 and in the crotch 102. When the outer shell is formed from a single fabric that is folded, as is illustrated in FIGS. 8 and 9, the seam in the crotch is eliminated. The shell optionally has attached to its inside surface an absorber for absorption and containment of body exudates. The undergarment product is elastically stretchable in the waist direction. When so stretched in the waist, the garment simultaneously contracts in the direction perpendicular to the waist. The contraction in the direction perpendicular to the waist results in an elastic pull upwards in the area of the crotch and diagonally around the legs, which result in the undergarment providing its wearer with a good and comfortable fit.

Figure 1:
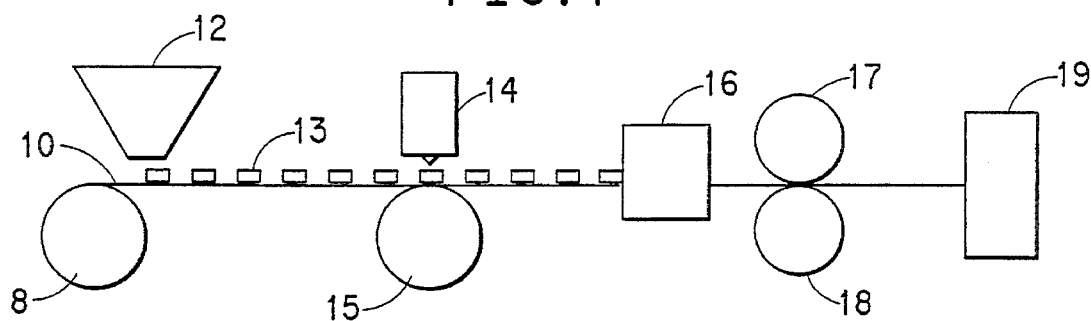
FIG. 1 is a flow diagram of a continuous process of the invention in which one layer of nonwoven elastic sheet 10 has absorbent structures 13 attached thereto and then is cut, folded and heat-seamed to form undergarments.
Figure 2:
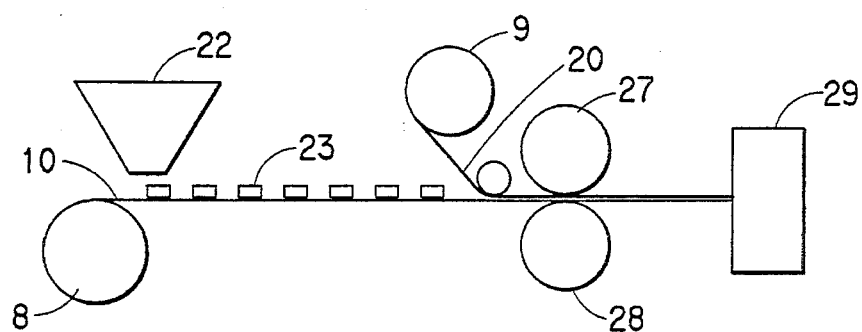
FIG. 2 is another flow diagram of a continuous process of the invention in which two layers of elastic nonwoven sheet 10, 20 are assembled with pre-folded absorbent structures 13 between the layers and then are simultaneously seamed and cut between heated roll 27 and patterned roll 28 to form undergarments.

Fabrics suitable for use as starting materials for the shell of undergarments made by the process of the current invention are conveniently supplied on rolls 10, 20, as indicated in FIGS. 1 and 2. Suitable starting fabrics are nonwoven elastic fabrics that comprise an array of parallel elastic strands incorporated with a deformable substrate. "Deformable substrate" as used herein means a layer that can be stretched by or contracted by the elastic strands, without tears or holes being formed in the deformable layer. The substrate itself is not necessarily elastic. The substrate can stretch inelastically when placed under tension and when under the contractive forces of the elastic strands, can pucker and/or buckle.

Substrates that are typically used in the elastic nonwoven fabrics fed to the process of the present invention include deformable nonwoven layers of substantially non-bonded fibers of textile dtex (i.e., about 1–22 dtex). Staple fibers or continuous filaments are suitable. Natural fibers or fibers of synthetic organic polymer are suitable. Among the various suitable deformable nonwoven layers are batts of carded fibers, cross-lapped batts, air-laid batts of filaments or fibers, nonwoven sheets of continuous filaments, lightly bonded spunbonded sheets, sheets of hydraulically entangled fibers and the like. Typical substrates weigh in the range of 15 to 65 grams per square meter.

As used herein, the term "substantially nonbonded", with regard to the deformable substrate when it is a nonwoven layer of natural or synthetic organic fibers of textile denier means that the fibers generally are not bonded to each other, as for example by chemical or thermal action. However, a small amount of point bonding or line bonding is intended to be included in the term "substantially nonbonded", as long as the bonding does not prevent the fibrous layer from satisfactorily stretching, contracting, and or buckling.

Typical elastic threads for use in the starting elastic nonwoven fabrics include elastomeric materials such as natural or synthetic rubber, spandex and the like. The threads may be covered or entangled with conventional nonelastic fibers (e.g., of nylon or polyester). Particularly preferred threads include spandex (e.g., Lycra® spandex yarn, sold by E. I. du Pont de Nemours and Co.) which has high elongation and high retractive power.

The elastic threads can be incorporated with the deformable substrate in any of several conventional ways. The threads may be attached to the substrate by stitching, intermittent gluing, continuous or intermittent thermal bonding, ultrasonically bonding, hydraulic entanglement and the like. The strands can be part of a network or simply a parallel array. The number of parallel strands in the network or array is in the range of 1 to 8 per centimeter. A preferred method for incorporating the elastic threads is by stitchbonding with a stitch frequency usually in the range of 1 to 8 stitches per centimeter, preferably 2 to 5. Simple stitch patterns are preferred, such as chain stitches or tricot stitches or a combination thereof. For economy, lightweight substrates and a minimum amount of elastic thread are preferred. Suitable general methods for preparing stitchbonded fabrics are disclosed in my earlier U.S. Pat. Nos. 4,773,238 and 4,998,421. Some stitchbonded fabrics can be used directly as a starting elastic nonwoven sheet for the process of the present invention. However, most stitchbonded fabrics, to be useful as starting elastic nonwoven elastic fabrics of the process of the invention, require a pretreatment, such as a heat setting treatment as shown in Example I below for Fabrics 1–5.

Elastic nonwoven fabrics suitable for use as starting materials in the process of the present invention have an elastic stretch of at least 70%, preferably in the range 100 to 250%, in the direction that will eventually become the waist portion of the undergarment. The elastic stretch of the starting fabric is accompanied by a simultaneous contraction of at least 20%, preferably in the range of 25 to 60%, in the direction perpendicular to the direction of elastic stretch. In contrast to many stitchbonded elastic fabrics, which can be stretched elastically without simultaneous contraction until the fabric has been stretched considerably above 100%, elastic stitchbonded fabrics suitable for use in the process of the invention, when stretched 70%, have a simultaneous contraction of at least 20%. Methods for determining the stretch, contraction and contraction at 70% stretch are given hereinafter.

Figure 3:
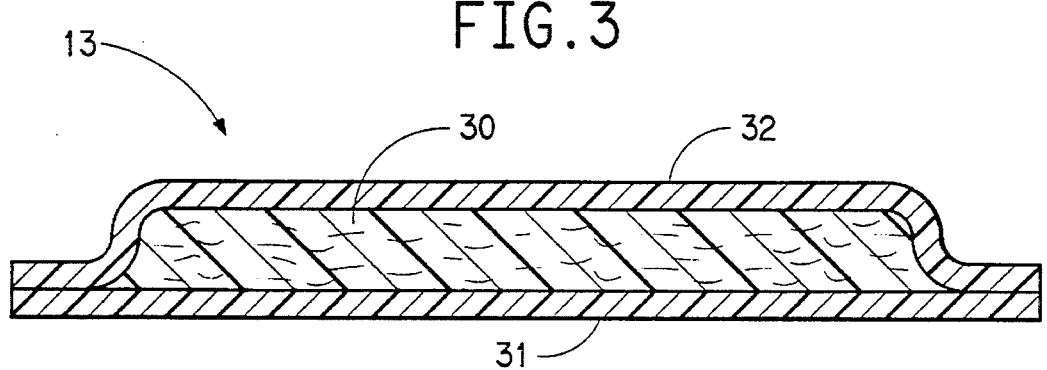
FIGS. 3 and 4 are respectively cross-sectional and plan view representations of an absorber 13 or 23 before being folded.
Figure 4:
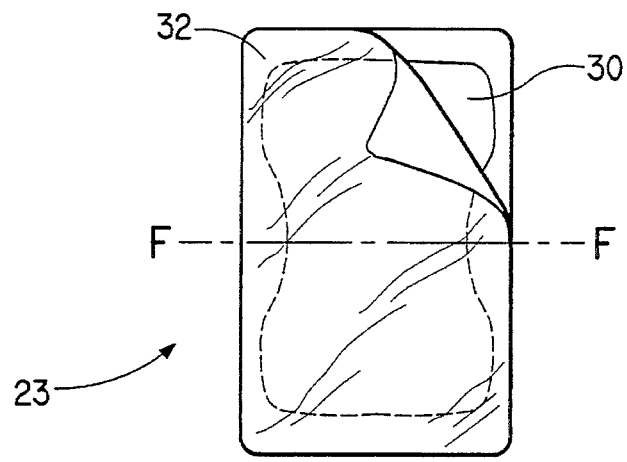

The undergarment made by the process of the present invention may include an optional conventional component, referred to herein as an "absorber", for absorbing and retaining body exudates. As illustrated in FIGS. 3 and 4, a typical absorber comprises an absorbent core 30 sandwiched between a liquid-permeable body-side liner 32 and a liquid-impermeable barrier layer 31. Materials suitable as liquid permeable body-side liners include nonwoven sheets and perforated films. Preferred absorbent core materials are absorbent fibers, such as comminuted woodpulp or cotton linters, hydrogels and the like. The absorbers can be of various shapes.

As illustrated in the flow diagram of FIG. 1, absorber 13, supplied from feeder 12, is placed on sheet 10, supplied from roll 8. The absorbers are attached to the sheets by means not shown. For the process of FIG. 1, absorbers 13 are fed flat (i.e., as shown in FIG. 4, not folded). For the process of FIG. 2, absorbers 23 are fed pre-folded along midline F—F shown in FIG. 4. The absorbers are attached in such a manner that starting sheets 10, 20 (supplied from rolls 8, 9, respectively) are free to stretch in the direction of the waistline while simultaneously contracting in the direction perpendicular to the waist. Preferably, the attachment of absorber 13 or 23 to the outer shell permits at least 75 percent of the elastic outer shell to stretch in the direction of the waistline while simultaneously contracting in the direction perpendicular to the waist. Various attachment means can be used such as heat or pressure activated adhesives, glues, thermal or ultrasonic bonding and the like. Preferably, the absorbers are adhered with these means to the sheet so that the adhesive attachment forms what in plan view would appear as a cross of small width along the midlines of the absorber. The adhesive is applied to the absorber, on the outside of the liquid-impervious layer. The area of the adhesive can be increased to reinforce the attachment in the region that is to become the crotch. Various other adhering configurations can be employed. Usually the corners of the absorber are free of adhesive so that the shell fabric can expand or contract without hindrance in the waist area.

Figure 5:
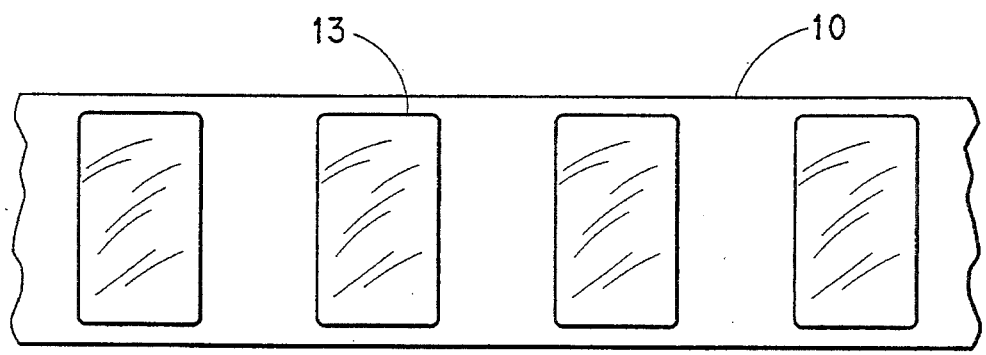
FIG. 5 illustrates for the process of FIG. 1 the position of absorbers 13 on elastic nonwoven sheet 10 immediately after the absorber is positioned on and attached to the sheet.
Figure 6:
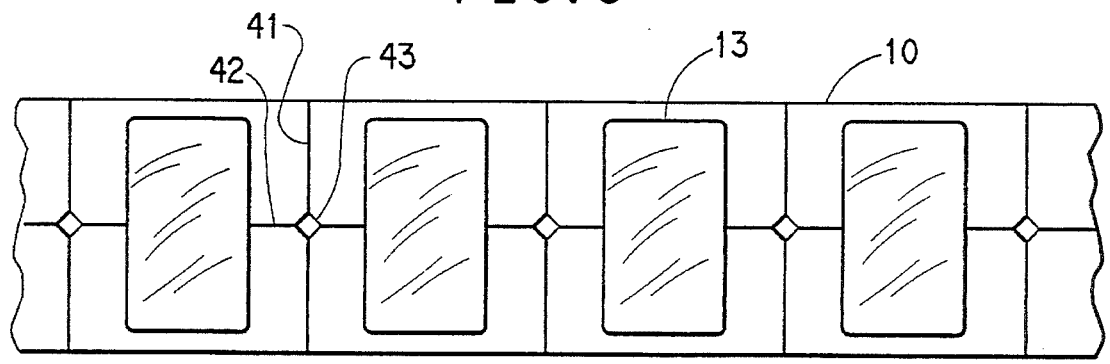
FIG. 6 illustrates for the process of FIG. 1 the cuts made in sheet 10 prior to the folding operation.
Figure 7:
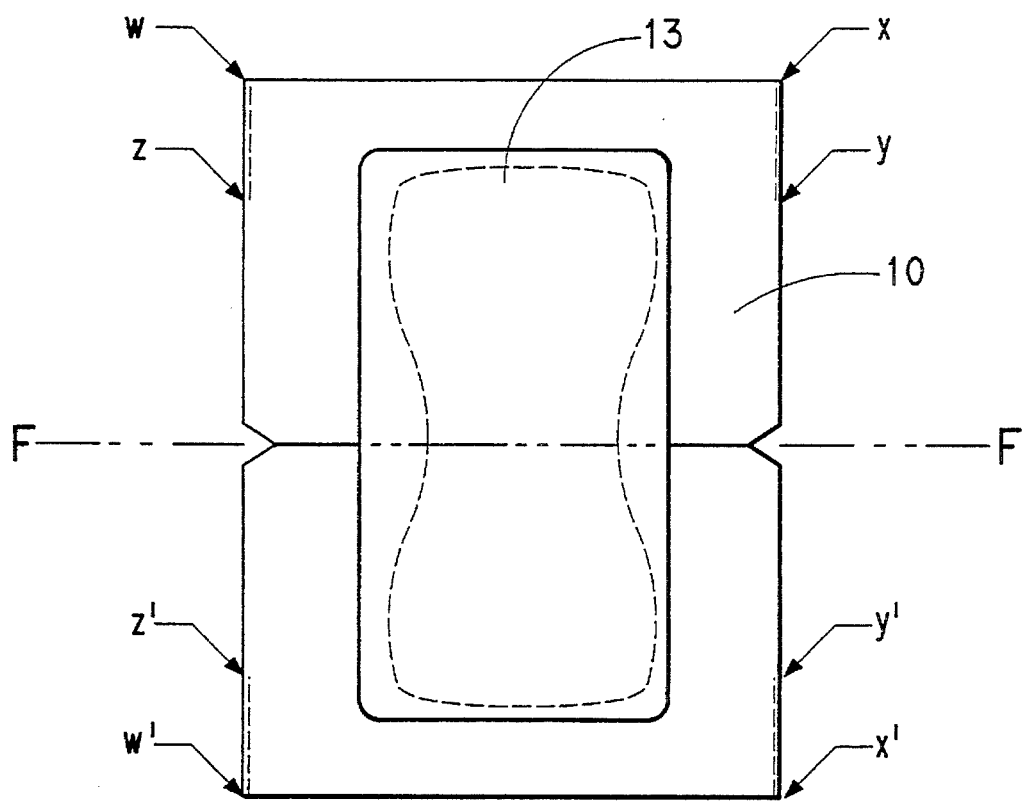
FIGS. 7 and 8 are respectively plan views of the garments immediately before and after folding and seaming.

In the process of FIG. 1, sheet 10, with absorbers 13 thereon, (see FIG. 5) are advanced to a cutting station which comprises backup roll 15 and cutting and slitting device 14. Device 14 can be a heated patterned roll, an ultrasonic cutter, a laser cutter or one of many other conventional devices. The cutting station can also supply the heat and or pressure necessary to adhere absorber 13 to sheet 10. The various cuts made in sheet 10 are shown in FIG. 6, wherein 41 designates slits made to form longitudinal edges of the garment, 43 a notch at the middle of the edges of the flat pattern, and 44 slits that proceed from notches 43 to the edge of absorber 13. FIG. 7, is a larger plan view of an individual garment cut from sheet 10 with absorber 13 in place the garment. Line segments wz and w'z' and line segments xy and x'y' represent edges that will be seamed together as shown in FIG. 8 after the diapers are folded along midline F—F by folding device 16 and passed between heated and patterned rolls 17, 18. Other conventional methods of seaming also are suitable for use in the process of the invention, such as adhesive bonding, ultrasonic bonding and the like.

Figure 10:
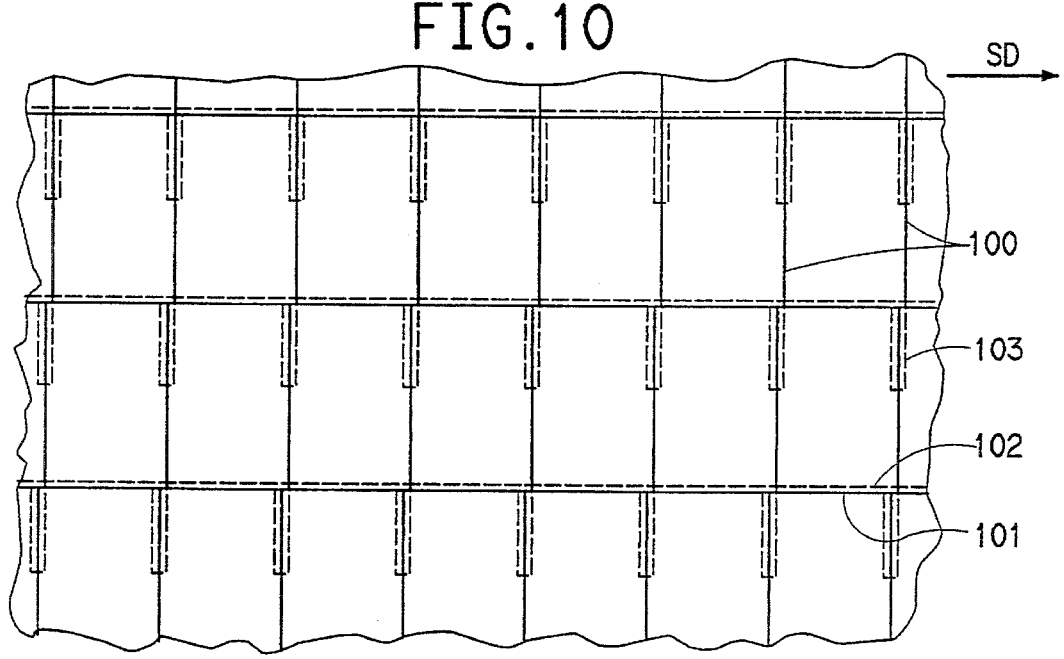
FIG. 10 illustrates for the process of FIG. 2 multiple units immediately after bonding and slitting rolls 27, 28 (with absorbers 23 omitted) and indicates the positions of the slits for leg openings 100 and waist opening 101 and the bonded seams that unite overlying sheets 10, 20 at the crotch 102 and sides 103.

In the process of the invention illustrated in FIG. 2, after absorbers 23 have been placed on sheet 10 by feeder 22, with the absorbers folded in half so that the liquid impervious film is in face to face contact with sheet 10, sheet 20 is fed from roll 9 atop the absorber to form a layered assembly that is then passed into a seaming and cutting station represented by heated and patterned rolls 27, 28. The seaming and cutting station, as shown in FIG. 10, makes cuts 100 to form the sides and 101 to form the waist openings while simultaneously making seams 103 to attach sheets 10, 20 together at the garment sides and 102 at the crotch area. The arrow designated "SD" in FIG. 10 indicates the intended direction of the waist and the direction of elastic stretch in the fabric. FIG. 11 shows an individual rectangular garment lying flat as it would be fed into packages 29. FIG. 12 shows the individual garment as it would appear on a torso, stretched in the waist and contracted in the direction perpendicular. For simplicity the optional absorber has been omitted from FIGS. 10, 11 and 12.

The process of the invention was described thus far with regard to starting sheets that are of uniform construction. However, sheets having lanes of different stretch and contraction characteristics can also be employed in the process of the present invention. For example, a starting sheet can be used which has lanes of high elastic stretch in what is to be the waist direction (and simultaneously a high neck-in in the perpendicular direction) which lanes are separated by lanes of little or no stretchability. Uniform sheets having lanes of high stretch and contraction would meet the criteria for starting sheets of the process, but sheets with the characteristics of the other lanes would not. However, sheets having both types of lanes can be used satisfactorily in the process. The widths and positions of the lanes can be arranged so that a finished undergarment is produced effectively with two side panels, one on each side, each of which is highly stretchable and with a front and a back panel that is of low or no stretchability. As long as the side panels can exert sufficient stretch and simultaneous necking-in to perform the function intended for the uniform starting sheets of the present process, starting sheets having lanes of different elastic character can be employed.

TEST METHODS

The ability of a fabric, while under light load, to stretch in a given direction and to contract in the direction perpendicular thereto (i.e., the contraction sometimes referred to as "neck-in") are determined as follows. A sample measuring 4 inches wide by 4 inches long (20.2 by 20.2 cm) is cut in the longitudinal ("LD") and transverse ("TD") directions of a the fabric being tested. The sample is suspended from a 4-inch-wide clamp with a second 4-inch-wide clamp attached to the opposite side of the sample. A 10-lb (4.54 kg) load is suspended from the second clamp for 30 seconds and then removed. The extended length and the corresponding contracted mid-span width are measured while the weight is still suspended. The recovered length is measured after the load is removed. The percent elastic stretch, %S, was calculated by the following formula $$\%S = 100(L_e - L_r)/L_r$$

and the percent simultaneous contraction, %C, (% neck-in) was calculated from the formula $$\%C = 100(W_i - W_e)/W_i$$

wherein Le is the extended length under load, Lr is recovered length after load removal, Wi is the initial width (i.e., 4 inches or 10.2 cm) of the sample and We is the necked-in width (i.e., while the sample was under load) at the mid-span of the sample. To determine whether an elastic fabric necks-in at least 20% when the fabric is stretched 70%, the above-described test is repeated with another sample of the fabric, except that as soon as the sample clamps have reached a distance of 6.8-inches (17.3-cm) apart, further separation of the clamps is stopped and the width in cm, w, of the stretched fabric sample is measured at its narrowest place. Thusly stretched samples having a measured width of no greater than 3.2 inches (8.1 cm) are of the invention; their contraction at 70% stretch is greater than 20%. The contraction at 70% stretch, %C(70), is calculated by the formula $$\%C(70) = 100(1 - w/10.2).$$

EXAMPLES

The invention is further illustrated by the following examples. Example I shows the fabrication of a series of fabrics that are suitable for use in the process of the present invention. Details of the fabrication of garments made with one of the fabrics by the process depicted in FIG. 1 are given in Example II.

Example I

Six fabrics were prepared by stitchbonding techniques for use as starting sheets in the process of the invention. Each of the first five illustrative fabrics was prepared on a "Liba" warp-knitting machine, with a deformable layer of Style 8017 "Sontara" spunlaced nonwoven fabric (sold by E. I. du Pont de Nemours & Co). weighing 0.7 oz/yd² (24.5 g/m²) and made from 100% polyester staple fibers of 1.35 denier (1.5 dtex) and ⅞-inch (2.2-cm) length, and with elastic strands that were made of covered spandex. The sixth fabric was similarly prepared except that the deformable web was a commercial 0.5 oz/yd² (17 g/m²) point bonded web of 1.5-den (1.7-dtex) 1.5-inch (3.8-cm) long polypropylene fibers sold by Scott Nonwovens of Landisville, N.J. The elastic stretch and simultaneous contraction characteristics of each sheet were determined in the longitudinal and transverse directions. The utility of each sheet for use in the undergarment manufacturing process of the invention is then evaluated. Table I summarizes the elastic stretch and simultaneous neck-in characteristics of each fabric.

Fabric 1 was prepared to be elastic in both the longitudinal and transverse directions. The spunlaced fabric was single-bar stitched with 1-0,1-2 tricot stitches at 12 gage (4/cm) and 14 stitches per inch (5.5/cm). The stitching thread was a nylon-covered "Lycra" spandex, Style L0523, sold by Macfield Texturing Inc. "Lycra" is a spandex yarn manufactured by E. I. du Pont de Nemours & Co. The stitching yarn was 140-den (154-dtex) "Lycra" covered with a 40-den (44-dtex) textured nylon. The fabric was finished by heat-setting on a tenter frame at 380 deg F. (193 deg C.) for 3 minutes. During finishing the fabric was allowed to shrink to 0.5 times its original length in the LD, while simultaneously being stretched to 1.2 times of its original width (i.e., the TD).

Fabric 2, which also has elastic stretch in the LD and TD, was made in the same manner as Fabric 1, except that the gage was 6 (2/cm).

Fabric 3, having LD elasticity, was constructed by stitching the "Sontara" deformable fabric with two bars, 9 stitches per inch (3.5 per cm) and 12 gage (4.7 per cm). The front bar was threaded the same elastic yarn as was used for the preceding samples and formed a 1-0,0-1 chain stitch. The back bar was threaded with a textured 70-den (77-dtex) polyester yarn and formed 1-0,2-3 tricot stitches. The fabric, during finishing on a pin tenter, was allowed to shrink to 0.4 times its original length LD, while simultaneously being stretched to 1.5 times its original width TD.

Fabric 4, having LD elasticity, was prepared in an identical manner to Fabric 3, except that there was no stitching provided by a second bar and the first bar made 6 stitches per inch (2.5/cm). The fabric was finished in the same way as was Fabric 3.

Fabric 5, having TD elasticity, was prepared by stitching the deformable layer with 70-den (77-dtex) polyester yarn on the back bar at 12 gage (4.5/cm), 12 stitches per inch (4.5/cm) to form 1-0,0-1 chain stitches and with bare 140-den (154-dtex) "Lycra" spandex on the front bar at 6 gage (2.4/cm) and 6 stitches per inch (2.4/cm) to form 1-0,1-2 tricot stitches. The fabric was finished at the same time and temperature conditions as the fabric 1, but was held taut in the LD as it was fed into the tenter frame, and was allowed to gather to approximately 0.8 times its original width in the TD.

Fabric 6, having TD elasticity, was prepared with only one bar forming 1-0,0-1 chain stitches at 4 stitches per inch (1.6/cm) and 4 gage (1.5/cm) in the deformable web. A stitching thread of 280-den (310-dtex) "Lycra" spandex covered with 70-den (77-dtex) polyester yarn was used.

The stretchability and neckin-in tendency of the fabrics were determined according to the test procedures described above. The results are summarized in Table I.

TABLE I

| Fabric | Longitudinal Test | | Transverse Test | |
|---|---|---|---|---|
| | % stretch | % neck-in | % stretch | % neck-in |
| 1 | 128 | 44 | 122 | 42 |
| 2 | 120 | 50 | 90 | 48 |
| 3 | 225 | 56 | 12 | 10 |
| 4 | 222 | 58 | 12 | 10 |
| 5 | 13 | 5 | 202 | 56 |
| 6 | 127 | 32 | nm | nm |

Note:
nm = no measurement made.

All six of the above-described fabric samples which could be stretched at least 70% in a given direction had a simultaneous contraction (at 70% stretch) in the direction perpendicular thereto of at least 20%. The data summarized in the table indicate that Fabrics 1 and 2 can be used with either their longitudinal direction or transverse direction parallel to the intended waist of the garment being made. However, Fabrics 3, 4 and 6 can be used only with their longitudinal direction in the waist direction. Fabric 5 can be used only with the transverse direction of the fabric parallel to the intended direction of the waist of the garment being fabricated. Fabrication of individual undergarments with these fabrics confirm these results.

Example II

Fabric 6 of Example I was used as a starting nonwoven elastic fabric in the process of the invention illustrated in FIG. 1. The starting sheet, measuring 21 inches (54 cm) in width was fed under uniform tension with about a two-fold stretch and with the width held constant. Absorbers, measuring about 16 inches (41 cm) in length and about 3.5 inches (9 cm) in width were attached to the sheet by a sprayed on glue in a cross configuration. The assembly was folded, cut and seamed to form the garments shown in FIG. 8 wherein the seam lengths wz and xy are 5.5 inches (14 cm) long.

I claim:

1. An improved process for making an anatomically form-fitting elastic undergarment that has a stretchable outer shell which is fabricated with a waist opening and two leg openings, the process comprising cutting and seaming operations performed on an elastic nonwoven sheet to form the outer shell for the garment and optionally attaching to its inner surface an absorbent structure for containment of body exudates, the improvement comprising the steps of stitchbonding with an elastic thread under tension a deformable nonwoven layer of weighing 17 to 65 grams per square meter and consisting essentially of substantially non-bonded fibers of 1 to 22 dtex to form an elastic stitchbonded nonwoven sheet comprising an array of parallel spaced-apart rows of elastic strands extending in a length direction of the sheet and being incorporated with the deformable nonwoven layer, heat setting the stitchbonded elastic nonwoven sheet while contracting the sheet in a first direction and stretching the sheet in a direction perpendicular to the first direction, to provide a heat-set sheet having an elastic stretch of at least 70% in the first direction and a simultaneous contraction in a direction perpendicular to the first direction of at least 20%, the contraction being at least 20% when the elastic stretch is 70%, feeding the heat-set stitchbonded elastic nonwoven sheet to the cutting and seaming operations, in a direction substantially parallel to or perpendicular to the first direction of the sheet, at substantially uniform tension across the width of the sheet, and selectively cutting and seaming the heat-set stitchbonded elastic nonwoven sheet in a flat trapezoidal or rectangular geometry with the first direction parallel to the waist direction of the undergarment being fabricated, to form the outer shell with the parallel rows of elastic strands being positioned in substantially the same direction throughout the shell.

2. A process in accordance with claim 1 wherein the elastic thread comprises spandex, the heat setting is performed while the stitchbonded elastic nonwoven sheet is contracted in the first direction and simultaneously expanded in the direction perpendicular to the first direction to provide the heat-set elastic nonwoven sheet with elastic stretch in the first direction in the range of 100 to 250% and simultaneous contraction in the direction perpendicular thereto in the range of 25 to 60%.

3. A process in accordance with claim 1 or 2 wherein the stitchbonding is performed with a stitch frequency in each row in the range of 2 to 5 per cm and the parallel rows are formed by series of chain stitches or by series of tricot stitches.

4. A process in accordance with claim 1, 2 or 3 wherein the cutting and seaming are performed simultaneously or in sequence by ultrasonic seaming and cutting techniques.

5. A process in accordance with claim 1, 2 or 3 wherein the cutting is performed laser cutting techniques.

6. A process in accordance with claim 1, 2 or 3 wherein the heat-setting step is carried out for about 3 minutes at a temperature of about 193° C.

* * * * *